United States Patent
Smith et al.

(10) Patent No.: US 8,106,201 B2
(45) Date of Patent: Jan. 31, 2012

(54) PROCESS FOR THE SYNTHESIS OF MORPHINANE COMPOUNDS AND INTERMEDIATES THEREOF

(75) Inventors: Craig Smith, Melbourne (AU); Stuart Purcell, Port Fairy (AU); Lucy Waddell, Launceston (AU); Nicholas Hayes, Port Fairy (AU); Jarrod Ritchie, Launceston (AU); Scott Brian Halliday, Edinburgh (GB); Melville Mitchell, Edinburgh (GB); George Scott Wilson, Edinburgh (GB)

(73) Assignees: Johnson Matthey Public Limited Company, London (GB); GlaxoSmithKline Australia Pty. Ltd., Port Fairy (AU)

(*) Notice: Subject to any disclaimer, the term of this patent is extended or adjusted under 35 U.S.C. 154(b) by 0 days.

(21) Appl. No.: 12/983,630

(22) Filed: Jan. 3, 2011

(65) Prior Publication Data

US 2011/0098474 A1    Apr. 28, 2011

Related U.S. Application Data

(60) Division of application No. 11/725,372, filed on Mar. 19, 2007, now Pat. No. 7,875,718, which is a continuation of application No. 10/572,973, filed as application No. PCT/AU2004/001297 on Sep. 22, 2004, now abandoned.

(30) Foreign Application Priority Data

Sep. 22, 2003 (AU) ................ 2003905153

(51) Int. Cl.
*C07D 498/12* (2006.01)
*C07D 498/02* (2006.01)
(52) U.S. Cl. .......................... 546/39; 546/44
(58) Field of Classification Search ............. 546/39, 546/44
See application file for complete search history.

(56) References Cited

U.S. PATENT DOCUMENTS

| 3,254,088 A | 5/1966 | Lewenstein et al. |
| 3,332,950 A | 7/1967 | Blumberg et al. |
| 5,112,975 A | 5/1992 | Wallace |
| 5,922,876 A * | 7/1999 | Huang et al. .............. 546/45 |

FOREIGN PATENT DOCUMENTS

| GB | 939287 | 10/1963 |
| WO | 0216367 | 2/2002 |

OTHER PUBLICATIONS

Proksa, "10-Hydroxythebaine," Arch. Pharm. Pharm. Med. Chem., 332, 369-370 (1999).
Iijima et al., "Studies in the (+)-Morphinan Series. 5. Synthesis and Biological Properties of (+)-Naloxone," Journal of Medicinal Chemistry, 1978, vol. 21, No. 4, pp. 398-400.
Krassnig et al., "Optimization of the Synthesis of Oxycodone and 5-Methyloxycodone," Arch. Pharm. Pharm. Med. Chem., 329, 325-326 (1996).
von Braun, "Die Einwirkung von Bromcyan auf tertiare Amine," J. Chem. Ber., 1900, 33, pp. 1438-1452.
Cooley et al., "Amine Dealkylations with Acyl Chlorides," Synthesis, 1989, pp. 1-7.
Lindner et al., "Demethylierung von Codein zu Norcodein Durch Sensibilisierte Photooxygenierung," Tetrahedron Lett., 1972, 17, pp. 1705-1706.
Santamaria et al., "Electron-Transfer Activation. Photochemical N-Demethylation of Tertiary Amines," Tetrahedron Lett., 1989, 30, pp. 2927-2928.
Lopez et al., "Photooxidation of Thebaine. A Route to 14-Hydroxymorphinones and Hydrodibenzofuran Analogs of Methadone," Tetrahedron Lett., 1994, 35, pp. 5727-5730.

* cited by examiner

*Primary Examiner* — Charanjit Aulakh
(74) *Attorney, Agent, or Firm* — RatnerPrestia

(57) ABSTRACT

This invention relates to intermediates useful in the preparation of opiate alkaloids, particularly morphinane compounds. The invention also relates to processes for preparing such intermediates and to processes which utilise such intermediates in the synthesis of morphinane compounds.

8 Claims, No Drawings

PROCESS FOR THE SYNTHESIS OF MORPHINANE COMPOUNDS AND INTERMEDIATES THEREOF

CROSS-REFERENCE TO RELATED APPLICATIONS

This application is a divisional application of U.S. patent application Ser. No. 11/725,372, filed Mar. 19, 2007 now U.S. Pat. No. 7,875,718, which is a continuation of U.S. patent application Ser. No. 10/572,973, filed Mar. 22, 2006, which is the U.S. National Phase of PCT International Application No. PCT/AU2004/001297, filed Sep. 22, 2004, and claims priority of Australian Patent Application No. 2003905153, filed Sep. 22, 2003, the entire disclosures of all of which are expressly incorporated herein by reference in their entirety for all purposes.

FIELD OF THE INVENTION

This invention relates to intermediates useful in the preparation of opiate alkaloids, particularly morphinane compounds. The invention also relates to processes for preparing such intermediates and to processes which utilise such intermediates in the synthesis of morphinane compounds.

BACKGROUND OF THE INVENTION

The opiate alkaloids obtained from poppy plants of the family *Papaveraceae* include some of the most powerfully acting and clinically useful drugs in the depression of the central nervous system. Exemplary opiates include morphine (1), codeine (2), heroin (3), thebaine (4) and oripavine (5).

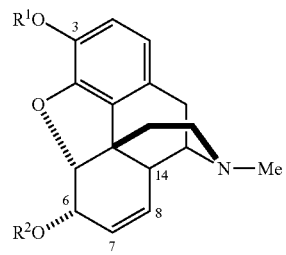

(1) $R^1 = R^2 = H$
(2) $R^1 = Me, R^2 = H$
(3) $R^1 = R^2 = MeC(O)$

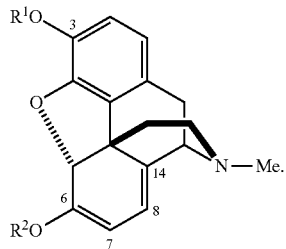

(4) $R^1 = R^2 = CH_3$
(5) $R^1 = H, R^2 = Me$

The fundamental ring system common to each of these compounds is the morphinane skeleton, depicted in formula (A). Compounds containing this skeleton are collectively referred to herein as morphinanes.

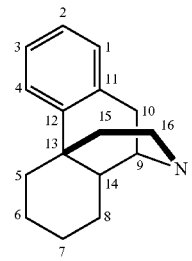

(A)

Morphine, codeine and heroin are characterised by a double bond at the 7-position ($\Delta^7$-morphinanes) while thebaine and oripavine possess a 6,8-diene system ($\Delta^6,\Delta^8$-morphinanes).

Morphine and codeine are principally used as analgesics but also find use as agents for inducing sleep in the presence of pain, easing dyspnea and as an anti-tussive. Despite its valuable clinical properties, morphine has a number of negative aspects as it also depresses respiration and increases the activity and the tone of the smooth muscles of the gastrointestinal, biliary and urinary tracts causing constipation, gallbladder spasm and urinary retention. In addition, if administered to a patient over a period of time, the patient develops a tolerance to the analgesic effect so that the dosage must be increased to obtain the same level of pain relief.

Heroin displays better lipid solubility than either morphine or codeine which allows for easy passage across the blood-brain barrier. It is this effect which is the primary reason heroin is so sought after as a recreational drug. When administered intravenously "users" experience an intense feeling of pleasure and dulling of pain. The problem however with heroin, morphine and related compounds is that in combination with the euphoric effect a physical dependence can develop.

Extensive efforts have been directed towards the semi-synthesis of second generation morphine-like molecules which retain the analgesic properties but avoid the undesirable addictive side effects. For example, replacement of the N-methyl group of morphine with an N-allyl group provides nalorphine which acts as a narcotic antagonist to reverse many of the undesirable side effects of morphine. Substitution of other groups such as methallyl, propyl, isobutyl, propargyl or cyclopropargyl, methylcyclopropyl, and methylcyclobutyl also produce substances that are narcotic antagonists.

Other second generation derivatives of natural opiates include the 14-hydroxy opiate antagonists, such as naltrexone (6), naloxone (7), and 14-hydroxynormorphinone (Nor14-OH) (8).

Naloxone (also known as Narcan) is routinely administered to patients suffering from opiate overdose (for instance, heroin overdose). It counteracts the effects of overdose by competitive inhibition at the opioid receptor sites. In the absence of other opioids, naloxone exhibits essentially no pharmacological activity. Naltrexone (also known as Tecan) is used in the detoxification of opiate addicts. 14-Hydroxynormorphinone is a synthetically valuable intermediate in the production of naloxone and naltrexone.

Accordingly, the 14-hydroxy opiates are pharmacologically important derivatives. The present invention is directed to processes and novel intermediates useful in the manufacture of 14-hydroxy opiates.

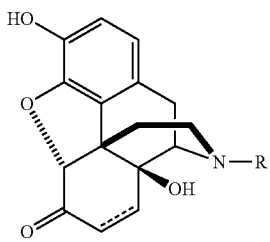

(6) R = cyclopropylmethyl, where ≡≡≡≡ is a single bond
(7) R = allyl, where ≡≡≡≡ is a single bond
(8) R = H, where ≡≡≡≡ is a double bond The industrial preparation of these second generation 14-hydroxy compounds presents some common but challenging problems. One problem common to the synthesis of many of these compounds is the removal of the N-methyl substituent present in naturally occurring opiate starting materials such as morphine, codeine, thebaine and oripavine. A second problem common to any synthetic approach to the 14-hydroxy opiates is the introduction of the 14-hydroxy group.

N-Demethylation of tertiary amines was traditionally achieved using cyanogen bromide in the von Braun reaction (von Braun, *J. Chem. Ber.*, 1900, 33, 1438). Limited yields and the toxicity of cyanogen bromide have seen this reaction largely replaced by chloroformate reagents (Cooley, J. H.; Evain, E. J. *Synthesis*, 1989, 1). Certain chloroformates, such as vinyl chloroformate, generally N-demethylate in high yield and the resultant carbamates are readily cleaved to afford the corresponding secondary amines. Unfortunately this reagent is very expensive, and thus, its applicability to larger scale processes is limited. Some photochemical procedures have been developed for the cleavage of N-methyl amines (Lindner, J. H. E.; Kuhn, H. J.; Gollnick, K. *Tetrahedron Lett.*, 1972, 17, 1705, Santamaria, J.; Ouchabane, R.; Rigaudy, J. *Tetrahedron Lett.*, 1989, 30, 2927, Lopez, D.; Quinoa, E.; Riguera, R., *Tetrahedron Lett.*, 1994, 35, 5727), but these methods have not seen widespread use.

In addition to this WO 02/16367 discloses a multistep complimentary sequence which includes N-demethylation and oxidation of a $\Delta^7$-morphinane compound to the $\Delta^6,\Delta^8$-morphinane compound. In the reported procedure, demethylation is achieved by initial oxidation of the N-methyl morphinane to form the N-oxide morphinane which is then treated with a Fe(II) based reducing agent. The oxidation of the $\Delta^7$-morphinane to the diene is reported as a separate reaction and is facilitated through the use of γ-MnO$_2$. Both of these procedures are complicated by work-up procedures which are inefficient on large scales. These work-up steps are required in both the N-demethylation and oxidation steps in order to separate the desired morphinanes from the respective Fe or Mn reagents after the respective reactions are completed.

Traditionally, the 14-hydroxy group has been introduced by the oxidation of $\Delta^6,\Delta^8$-morphinanes. For example, GB 939287 describes the oxidation of thebaine (4) in formic acid with 30% hydrogen peroxide at 40-50° C. to give 14-hydroxycodeinone. Interestingly, the commonly used procedures have usually only involved the oxidation of $\Delta^6,\Delta^8$-morphinanes which have a protected 3-hydroxy group. Consequently in the preparation of commercially valuable 14-hydroxy opiates, such as naloxone and naltrexone, an additional step would be required to remove the protective group. Oripavine, which is extracted from the poppy plant in low yields and has an unprotected 3-hydroxy group, has not been widely used as a starting material for the commercial production of 14-hydroxy opiates. Although oripavine is naturally less abundant than either morphine and codeine, its present lack of utility means that there is no real shortage of this naturally occurring opioid. Accordingly, it would be desirable to be able to use oripavine as a starting material for the production of 14-hydroxy opiates.

SUMMARY OF THE INVENTION

In one aspect the present invention provides a method for preparing a 6-oxo-14-hydroxy $\Delta^7$-morphinane comprising oxidising a 6-methoxy-N-methyl-$\Delta^6,\Delta^8$-morphinane for a time and under conditions sufficient to form a 6-oxo-14-hydroxy-N-methyl-$\Delta^7$-morphinane-N-oxide and converting the formed N-oxide to the 6-oxo-14-hydroxy-$\Delta^7$-morphinane.

In another aspect the present invention provides a method for converting a 6-oxo-14-hydroxy-N-methyl-$\Delta^7$-morphinane-N-oxide to a 6-oxo-14-hydroxy-$\Delta^7$-morphinane comprising subjecting the N-oxide to reducing conditions to ring close the N-methyl group with the 14-hydroxy group forming an oxazolidine ring, and hydrolysing the ring closed oxazolidine product to form the 6-oxo-14-hydroxy-$\Delta^7$-morphinane.

In a further aspect of the invention there is provided a compound having the following modified morphinane skeleton:

(B)

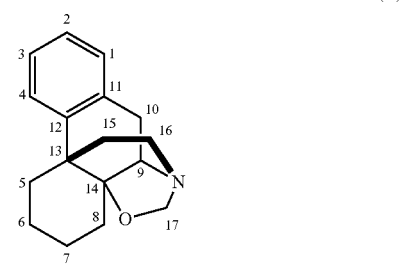

In yet another aspect the invention provides a method of preparing a morphinane compound having a modified morphinane skeleton (B) comprising treating a 6-oxo-N-methyl-14-hydroxy-$\Delta^7$-morphinane-N-oxide with an Fe(II) reducing agent for a time and under conditions sufficient to ring close the N-methyl group with the 14-hydroxy group.

In another aspect of the invention there is provided a method for preparing N-alkyl or N-alkenyl 6-oxo-14-hydroxy morphinanes comprising:

oxidising a 6-methoxy-N-methyl-$\Delta^6,\Delta^8$-morphinane for a time and under conditions sufficient to form a 6-oxo-14-hydroxy-N-methyl-$\Delta^7$-morphinane-N-oxide, converting the formed N-oxide to a 6-oxo-14-hydroxy-$\Delta^7$-morphinane, reducing the $\Delta^7$ double bond to form a 6-oxo-14-hydroxy morphinane, and subjecting the 6-oxo-14-hydroxy-morphinane to N-alkylation to introduce the N-alkyl or N-alkenyl substituent.

DETAILED DESCRIPTION OF THE INVENTION

The processes according to the present invention are capable of being performed using naturally isolatable $\Delta^6,\Delta^8$-morphinanes like oripavine (4) and thebaine (3) as starting materials. Preferably the 6-methoxy-N-methyl-$\Delta^6,\Delta^8$-morphinane is a compound of formula I:

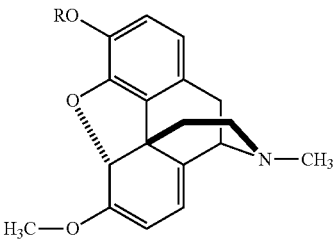

where R is H, $C_1$-$C_6$ alkyl, benzyl or acyl.

The term "$C_1$-$C_6$ alkyl" as used herein refers to a straight chain or branched alkyl group having from 1 to 6 carbon atoms. Examples of suitable alkyl groups include methyl, ethyl, propyl, isopropyl and n-butyl.

The term "acyl" as used herein refers to a group of formula RNC(=O)—, where RN is generally an $C_1$-$C_6$ alkyl group. An example of acyl group is an acetyl group.

It is also possible for R to represent an hydroxy protecting group, although protection of the hydroxy group is not necessary in the process of the present invention.

There are also many reported synthetic approaches to 6-methoxy-N-methyl-$\Delta^6,\Delta^8$-morphinanes and both synthetic and naturally derived compounds can be incorporated into the processes of the present invention. The preferred $\Delta^6,\Delta^8$-morphinanes to be used in the process of the present invention are oripavine and thebaine. Oripavine, however, is the most preferred starting material.

The process according to the present invention allows for the conversion of 6-methoxy-N-methyl-$\Delta^6,\Delta^8$-morphinanes to 6-oxo-14-hydroxy-N-methyl-$\Delta^7$-morphinane-N-oxides in a single step. That is, in a single step, the 14-hydroxy group is introduced, the N-methyl group is oxidized to the corresponding N-methyl oxide, the 6-methoxy is converted to 6-oxo group and the $\Delta^6,\Delta^8$ conjugated diene is converted to $\Delta^7$ double bond. The 6-oxo-14-hydroxy-N-methyl-$\Delta^7$-morphinane-N-oxide may be a compound of formula II:

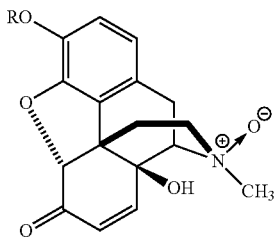

where R is H, $C_1$-$C_6$ alkyl, benzyl or acyl.

This oxidation may be carried out by treating the 6-methoxy-N-methyl-$\Delta^6,\Delta^8$-morphinane with hydrogen peroxide ($H_2O_2$) in the presence of formic acid or other suitable carboxylic acids such as, for instance, acetic acid. The preferred concentration of hydrogen peroxide used in the oxidation is between 30-50% by weight in water. More preferably, the hydrogen peroxide is at a concentration of 50% by weight in water. Preferably the 6-methoxy-N-methyl-$\Delta^6,\Delta^8$-morphinane is treated with the hydrogen peroxide in molar excess, for example with 2-5 equivalents, more preferably at least 3 equivalents.

The oxidation process is preferably carried out in the presence of formic acid. Preferably the formic acid concentration is between 30-96% by weight in water. More preferably the concentration is between 35-55% and even more preferably 40-50%. Most preferably the formic acid is at a concentration of 45%.

It is preferred that the reaction temperature of the oxidation is carried out at below 50° C. Preferably the reaction is carried out at a temperature from 20-40° C., however a constant reaction temperature of ~20° C. is particularly preferred.

In a preferred embodiment oxidation of the 6-methoxy-N-methyl-$\Delta^6,\Delta^8$-morphinane to the 6-oxo-14-hydroxy-N-methyl-$\Delta^7$-morphinane-N-oxide is performed in the presence of a solvent. Preferably the solvents are polar solvents, which may be protic or aprotic. Preferably the solvent is an alcohol, for example methanol, ethanol, propanol, iso-propanol, etc. Most preferably the solvent is ethanol.

In another preferred embodiment of the oxidation process the 6-methoxy-N-methyl-$\Delta^6,\Delta^8$-morphinane is dissolved in a mixture of formic acid and the solvent prior to the addition of the hydrogen peroxide.

The reaction should be carried out for a time which allows for the formation of the desired N-oxide. This time may depend on the amount of material being treated, the amount, nature and concentration of the oxidizing agent present and the temperature at which the reaction is carried out. Monitoring the reaction by chromotographic means, such as thin layer chromatography (TLC) will allow the skilled practitioner to determine the completeness of the reaction. Suitably, the oxidation reaction is carried out for at least 30 minutes, although more usually it will be for at least 1 or 2 hours.

The oxidation of the 6-methoxy-N-methyl-$\Delta^6,\Delta^8$-morphinane to the 6-oxo-14-hydroxy-N-methyl-$\Delta^7$-morphinane-N-oxide may be followed by an isolation step before conversion to the 6-oxo-14-hydroxy-$\Delta^7$-morphinane. The isolation of the 6-oxo-14-hydroxy-N-methyl-$\Delta^7$-morphinane-N-oxide may be achieved by any suitable means. For example, upon completion, the crude reaction mixture may be neutralized to a pH of about 7. This can be effected by the addition of a suitable base, for example, sodium or potassium hydroxide, potassium carbonate, etc. In a preferred embodiment, the oxidation reaction mixture is neutralized with a sodium hydroxide solution at a rate which ensures that the reaction temperature reaches 55° C. This is preferably done over a period of time (for example 2 hrs) at which time the reaction is allowed to continue for a further 1-2 hr period before being cooled. After this time the crude N-oxide product (compound of formula II) can be collected as a solid. This crude solid may be subject to further purification steps (eg. washing with water and/or ethanol) or it may be reduced in crude form.

The 6-oxo-14-hydroxy-N-methyl-$\Delta^7$-morphinane-N-oxide is then converted to 6-oxo-14-hydroxy-$\Delta^7$-morphinane by performing an N-demethylation. This is generally done by treating it with a reducing agent. Suitable reducing conditions are outlined in WO02/16367 which is incorporated herein by reference. Exemplary reducing agents include Fe (II) based agents such as $FeSO_4$, $FeCl_2$ or Fe-porphrin complexes. Preferably when the reduction is to be carried out on a plant scale the reaction is preformed at a temperature of around 10° C. The reaction can be monitored by TLC to determine the completeness of the reduction (N-demethylation). In order to remove any excess Fe(II) species the reaction mixture may be subjected to work-up step(s) which may, for instance, involve addition of ammonium hydroxide and subsequent filtering.

The 6-oxo-14-hydroxy-$\Delta^7$-morphinane will generally be a compound of formula III:

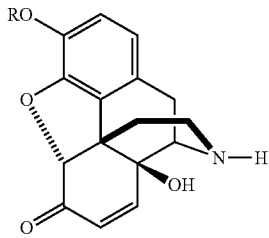

III where R is H, $C_1$-$C_6$ alkyl, benzyl or acyl.

It has now been surprisingly found that when the 6-oxo-14-hydroxy-N-methyl-$\Delta^7$-morphinane-N-oxide is treated with a Fe(II) based reducing agent and formic acid, a novel product having a morphinane skeleton

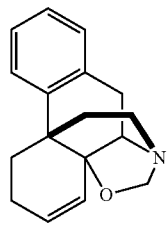

(B)

is formed in good yield. Such oxazolidines may be easily separable from the crude reaction mixture as an insoluble precipitate and can be readily hydrolyzed to prepare a 6-oxo-14-hydroxy-$\Delta^7$-morphinane. The oxazolidine compound will generally be of formula IV:

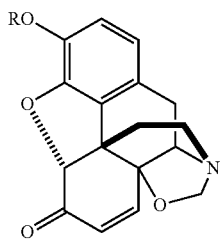

IV where R is H, $C_1$-$C_6$ alkyl, benzyl or acyl.

Structural elucidation studies, including 2-D NMR (1H COSY, HMQC and HMBC), have indicated that the intermediate has this structure.

In a preferred embodiment of this process the 6-oxo-14-hydroxy-N-methyl-$\Delta^7$-morphinane-N-oxide is treated as a slurry in methanol with $FeSO_4$, whereby formic acid is then added which forms the oxazolidine compound of formula IV as an acid insoluble precipitate.

One particular advantage in the formation of the oxazolidine compound is that its acid insolubility makes it easy to separate from the iron reducing agent and the crude reaction mixture. This is generally achieved by a simple filtration step. The crude oxazolidine intermediate can then be immediately hydrolyzed or subjected to a further washing step (for example with methanol). This process is extremely beneficial in the production of kilogram scales of 14-hydroxy opiates as the tedious work-up steps generally required to remove the iron reducing agent are avoided.

Conversion of the oxazolidine compound to the 6-oxo-14-hydroxy-$\Delta^7$-morphinane by hydrolysis can be achieved by treating the oxazolidine compound with a strong acid. Preferred strong acids include, hydrochloric acid, sulphuric acid, hydrobromic acid, phosphoric acid, etc. Preferably the compound of formula IV is hydrolyzed with hydrochloric acid. More preferably the hydrolysis is preformed at elevated temperatures. In a preferred embodiment hydrolysis is conducted with a strong acid followed by ammonia at an elevated temperature.

As stated earlier, the 6-oxo-14-hydroxy-$\Delta^7$-morphinane is an important intermediate for the preparation of 14-hydroxy opiates, especially those which have a non-methyl N-substituent, for example naltrexone (6) and naloxone (7). Processes for converting 6-oxo-14-hydroxy-$\Delta^7$-morphinanes into other useful morphinane compounds are described in the literature.

The compound of formula III where R=H is of particular importance in the preparation of compounds (6) and (7) as its use alleviates the need for a further deprotection step.

The production of these compounds can be achieved in two steps from a compound of formula III. Such a synthesis would include an initial reduction step, for example using catalytic hydrogenation, to afford the dihydro derivative (6-oxo-14-hydroxy-morphinane), followed by N-alkylation with a suitable alkylating agent, such as L-RN where L is a leaving group and RN is an alkyl or alkylene group. Such a process is illustrated in Scheme 1 below.

Scheme 1

Formula III

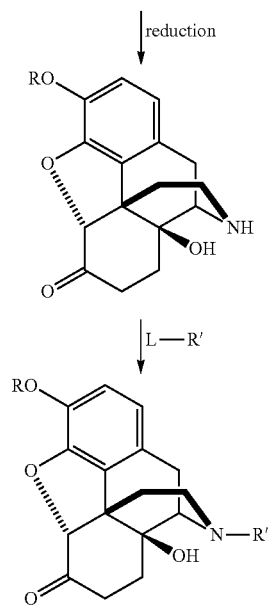

As indicated above an example of a treatment to reduce the double bond at the 7-position involves catalytic hydrogenation. GB 939,287 describes such a process in which platinum chloride is used as a catalyst in 10% acetic acid. U.S. Pat. No. 5,112,975, U.S. Pat. No. 5,922,876 and U.S. Pat. No. 5,922, 876 also disclose suitable methods for reducing the Δ⁷-double bond of compounds of formula III, and are incorporated herein by reference.

An example of an alkylation treatment would be the reaction of the N-demethylated compound with R'—Br and a base, such as $K_2CO_3$. Suitable N-alkylation conditions are disclosed in U.S. Pat. No. 3,254,088, U.S. Pat. No. 3,332,950 and U.S. Pat. No. 5,922,876 which are incorporated herein by reference. Exemplary R' groups include $C_{2-6}$ alkyl, such as straight chain, branched and cyclic isomers of ethyl, propylbutyl, isobutyl pentyl (all isomers), hexyl (all isomers), cyclopropylmethyl, (as found in naltrexone (5)) and cyclobutylmethyl (as found in nalbuphine and butorphanol), $C_{2-6}$ alkenyl residues such as alkyl (as found in nalorphine and naloxone (6)), and $C_{2-6}$ alkynyl, such as propargyl.

Examples of leaving groups include halogen, such as Br, Cl and I, mesylate, tosylate and triflate.

In an alternate preferred embodiment a 6-oxo-14-hydroxy-N-methyl-Δ⁷-morphinane can be first hydrogenated and subsequently oxidised to form the corresponding N-oxide. Hydrogenation to reduce the Δ⁷-double bond may be carried out in the presence of platinum or palladium catalysts under the standard hydrogenation conditions as discussed above. The N-oxide from this procedure may be reduced as mentioned previously to form an oxazolidine compound. The oxazolidine compound will generally be of formula V:

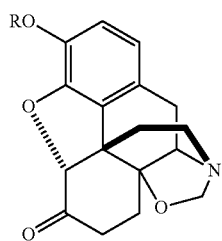

V where R is H, $C_1$-$C_6$alkyl, benzyl or acyl.

Hydrolysis of the oxazolidine and alkylation to form, for instance, naltrexone (6) and naloxone (7), may follow the synthetic route previously discussed.

Following the preparation of the N-alkyl or N-alkenyl 6-oxo-14-hydroxymorphinane it is possible to further modify the compound using known techniques to prepare further morphinane derivatives. For example, if the Δ⁷ double bond is not reduced, further chemistry can be performed on the α, β unsaturated keto moiety. The oxygen atom in the 3-position can be subjected to esterification, transesterification and etherification reactions using known techniques.

The reference to any prior art in this specification is not, and should not be taken as, an acknowledgment or any form of suggestion that that prior art forms part of the common general knowledge in Australia.

The invention will now be described with reference to the following examples which are intended only for the purpose of illustrating certain embodiments of the invention and are not to be taken as limiting the generality of the invention previously described.

EXAMPLES

Example 1 a) Oripavine Oxidation to 14-hydroxymorphinone-N-oxide (14-NO)

Formic acid 45% (100 L) is added to ethanol (100 L). Oripavine is dissolved in the acidic ethanol (100 kg/200 L). 50% hydrogen peroxide (70 L) is added and the temperature is maintained at 20° C. by cooling. After 2 hrs the reaction mixture is neutralised to pH 7 with the addition of 23% NaOH at a rate which ensures that the temperature of the reaction reaches 55° C. This is performed over 2 hrs. When this temperature is reached the mixture is allowed to react for a further 1-2 hrs. After this time the reaction mixture is cooled to 15° C. and solid material filtered. The filtered cake is washed with water (100 L/100 kg) and then with ethanol (80% yield); LC-MS m/z 316 (M+H)

b) Reduction of (14-NO) to Oxazolidine (Compound of Formula Iv, where R=H)

14-Hydroxymorphinone-N-oxide (14-NO) (4 kg) is added to 100 L of methanol (>98%). The resultant slurry is stirred for 5 minutes. To the slurry is added 0.8 kg $FeSO_4.7H_2O$ and the resultant mixture is vigorously stirred for about 5 minutes. After 2 minutes 15 L of 85% Formic acid is added and the resultant precipitate is immediately filtered after mixing complete. The precipitated oxazolidine is washed with methanol (55% yield); 13C NMR ($DCO_2D$) δ 25.4 (C10), 29.5 (C15), 45.8 (C16), 48.1 (C13), 65.7 (C9), 78.8 (C14), 84.0 (C17), 86.1 (C5), 120.4 (C1), 121.3 (C11), 122.0 (C2), 128.5 (C12), 136.6 (C9), 139.5 (C3), 142.6 (C8), 143.4 (C4), 196.6 (C6) ppm; $^1$H NMR ($DCO_2D$) δ 2.8 (m, 1H, H15), 3.5 (m, 1H, H15), 4.2 (m, 2H, H10, H16), 4.4 (m, 2H, H10, H16), 5.4 (d, 1H, H9), 5.7 (s, 1H, H5), 6.1 (dd, 2H, H17), 7.1 (d, 1H, H7), 7.45 (d, 1H, H1), 7.51 (d, 1H, H2), 7.60 (d, 1H, H8) ppm.

c) Hydrolysis of Oxazolidine to 6-oxo-14-hydroxy-Δ⁷-morphinane (Compound of Formula III, where R is H)

The oxazolidine (1 kg) is added to a solution of 25% ammonium hydroxide (0.96 L) in $H_2O$ (7.2 L). 30% Hydrochloric acid (1.65 L) is then added and the mixture is heated to 50° C. followed by the addition of activated carbon (0.025 kg). After 30 min the activated carbon is removed by filtration and the filtrate is stirred for a further 30 min. The pH is then adjusted to pH 9.0 with 25% ammonia and stirred for a further 15 hours at 50° C. After this time the mixture is cooled below 20° C. and the precipitate is filtered and washed with $H_2O$ (5 L) (85% yield); $^{13}$C NMR ($D_2O$/DCl) δ 25.2 (C15), 26.7 (C10), 37.3 (C16), 46.3 (C13), 56.6 (C9), 66.6 (C14), 86.1 (C5), 118.9 (C1), 121.3 (C2), 122.4 (C11), 128.9 (C12), 133.0 (C7), 138.8 (C4), 142.7 (C3), 147.9 (C8), 196.9 (C6) ppm.

Example 2 a) 14-hydroxycodeinone oxidation to 14-hydroxycodeinone-N-oxide tartrate

14-Hydroxycodeinone (20.0 g) was added to methanol (100 mL) followed by mCPBA (21.9 g, 50% wet). After stirring for 40 min, L(+)-Tartaric acid was added to pH 3.5 to precipitate 14-hydroxycodeinone-N-oxide tartrate which was collected by filtration (83% yield). LC-MS m/z 330 [M+H].

b) Reduction of 14-hydroxycodeinone-N-oxide tartrate to oxazolidine (Compound of Formula IV, where R=$CH_3$)

14-Hydroxycodeinone-N-oxide tartrate (14.8 g) was slurried in methanol (200 mL). $FeSO_4.7H_2O$ (2.0 g) was then added and the solution was stirred for 40 min. The product was collected by filtration and the solid was washed with methanol (40 mL) to yield the oxazolidine (~10% yield, ESI-MS m/z 312 [M+H]) as a mixture with 14-hydroxycodeinone.

Example 3 a) Benzylation of 14-hydroxymorphinane-N-oxide

14-Hydroxymorphinone-N-oxide (100 g) was slurried in ethanol (500 mL). $K_2CO_3$ (52.5 g) was then added followed by benzyl bromide (95.0 g). The resulting mixture was stirred at RT for 16 h then at 50° C. for 4 h. The solution was cooled to RT then filtered and the solid was washed with ethanol (200 mL). The solid was slurried in water (500 mL) for 30 min then was collected by filtration to yield 3-benzyl-14-hydroxymorphinone-N-oxide (78% yield). ESI-MS m/z 406 [M+H].

b) Reduction of 3-benzyl-14-hydroxymorphinone-N-oxide to oxazolidine (Compound of Formula IV, where R=benzyl)

3-Benzyl-14-Hydroxymorphinone-N-oxide (5.0 g) was slurried in methanol (100 mL). $FeSO_4.7H_2O$ (0.5 g) was then added and the solution was stirred for 15 min. The product was collected by filtration and the solid was washed with methanol (20 mL) to yield the oxazolidine (~15% yield, ESI-MS m/z 388 [M+H]) as a mixture with 3-benzyl-14-hydroxymorphinone.

Example 4 a) Oxymorphone Oxidation to Oxymorphone-N-oxide

Oxymorphone (4.0 g) was added to methanol (40 mL) followed by mCPBA (5.50 g, 50% wet). After stirring for 5 min oxymorphone-N-oxide was collected by filtration (75% yield). ESI-MS m/z 318 [M+H].

b) Reduction of Oxymorphone-N-oxide to oxazolidine (Compound of Formula V, where R=H)

Oxymorphone-N-oxide (2.0 g) was slurried in methanol (40 mL). $FeSO_4.7H_2O$ (0.4 g) was then added and the solution was stirred for 15 min. The product was collected by filtration and the solid was washed with methanol (15 mL) to yield the oxazolidine (~50% yield, ESI-MS m/z 300 [M+H]) as a mixture with oxymorphone.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

What is claimed:

1. An oxazolidine of formula IV:

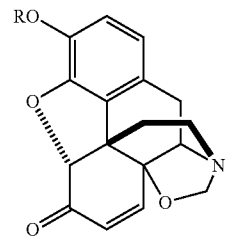

where R is H, $C_1$-$C_6$alkyl, benzyl or acyl.

2. An oxazolidine of formula IV according to claim 1 wherein R is H, $CH_3$ or benzyl.

3. An oxazolidine of formula IV according to claim 2 wherein R is H.

4. An oxazolidine of formula V:

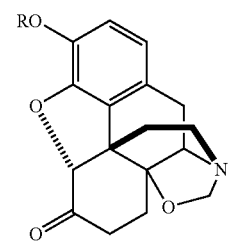

where R is H, $C_1$-$C_6$alkyl, benzyl or acyl.

5. An oxazolidine of formula V according to claim 4 wherein R is H or $CH_3$.

6. An oxazolidine of formula V according to claim 5 wherein R is H.

7. A method of preparing a morphinane compound having a modified morphinane skeleton of structure (B)

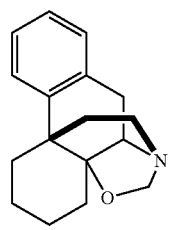

said method comprising treating a 6-oxo-N-methyl-14-hydroxy-$\Delta^7$-morphinane-N-oxide with an Fe(II) reducing agent for a time and under conditions sufficient to ring close the N-methyl group with the 14-hydroxy group.

8. A method according to claim 7 wherein the Fe(II) reducing agent is $FeSO_4$.

* * * * *